United States Patent [19]
Rutherford et al.

[11] Patent Number: 5,292,657
[45] Date of Patent: Mar. 8, 1994

[54] PROCESS FOR PREPARING ROTARY DISC FATTY ACID MICROSPHERES OF MICROORGANISMS

[75] Inventors: William M. Rutherford, Des Moines; Jack E. Allen, Boonville, both of Iowa; Herman W. Schlameus, San Antonio, Tex.; Donald J. Mangold, San Antonio, Tex.; William W. Harlowe, Jr., San Antonio, Tex.; Joseph R. Lebeda, Urbandale, Iowa

[73] Assignee: Pioneer Hi-Bred International, Inc., Des Moines, Iowa

[21] Appl. No.: 842,226

[22] Filed: Feb. 26, 1992

Related U.S. Application Data

[63] Continuation-in-part of Ser. No. 635,973, Dec. 31, 1990, abandoned.

[51] Int. Cl.$^5$ ............... C12N 1/00; C12N 11/02; C12N 1/20; A23L 1/28; B01J 13/02; A61K 9/16; A61K 9/14
[52] U.S. Cl. ............... 435/243; 435/252.1; 435/177; 435/174; 426/61; 264/4.3; 424/498; 424/484
[58] Field of Search ........... 435/243, 174, 177, 252.1, 435/252.9, 253.4, 255; 264/4.3; 426/61; 424/484, 498

[56] References Cited

U.S. PATENT DOCUMENTS

| | | | |
|---|---|---|---|
| 1,260,899 | 3/1918 | Harris | 424/93 |
| 2,369,218 | 2/1945 | Dick et al. | 167/78 |
| 3,856,699 | 12/1974 | Miyano et al. | 252/316 |
| 3,959,493 | 5/1976 | Baalsrud et al. | 426/2 |
| 4,332,790 | 6/1982 | Sozzi et al. | 424/38 |
| 4,352,883 | 10/1982 | Lim | 435/178 |
| 4,386,895 | 6/1983 | Sodickson | 425/5 |
| 4,675,140 | 6/1987 | Sparks et al. | 264/4.3 |
| 4,692,284 | 9/1987 | Braden | 264/4.3 |
| 4,710,379 | 12/1987 | Kawai et al. | 424/93 |
| 4,713,245 | 12/1987 | Ando et al. | 424/438 |
| 4,842,863 | 6/1989 | Nishimura et al. | 424/438 |
| 4,877,621 | 10/1989 | Ardaillon et al. | 424/498 |

FOREIGN PATENT DOCUMENTS 2016043 9/1979 United Kingdom.

OTHER PUBLICATIONS

Johnson et al., "A New Method for Coating Glass Beads for Use In Gas Chromatography of Chloropromazine and Its Metabolites", *J. of G. C.* Oct. 1965 345-347.

ATCC Catalogue of Bacteria & Bacteriophages, p. 79 (1989).

*Primary Examiner*—Douglas W. Robinson
*Assistant Examiner*—Susan M. Dadio
*Attorney, Agent, or Firm*—Zarley, McKee, Thomte, Voorhees & Sease

[57] ABSTRACT

A process for preparing fatty acid microspheres of microorganisms by rotary disc processing is disclosed. The process is designed to minimize heat risk to the microorganisms during production. Microsphere particles of fatty acid matrix containing microorganisms, preferably stearic acid encapsulated *Enterococcus faecium*, are also provided.

9 Claims, 5 Drawing Sheets

PROCESS FOR PREPARING ROTARY DISC FATTY ACID MICROSPHERES OF MICROORGANISMS

CROSS REFERENCE TO A RELATED APPLICATION

This application is a continuation-in-part of Ser. No. 07/635,973 entitled DRIED, ROTARY DISC FATTY ACID MICROENCAPSULATED BACTERIA, filed Dec. 31, 1990, now abandoned.

BACKGROUND OF THE INVENTION

It is known that certain microorganisms such as bacteria are potentially beneficial when added to animal feeds. For example, bacteria are beneficial in that they supply a natural intestinal microflora. Some companies offer for sale direct fed microbials which contain desirable bacteria. Direct fed microbials, however, do have some difficulty in maintaining a stable product. Typically, the direct fed microbial is used at a fairly small level, added to feed at perhaps a 1% level. However, unused direct fed microbial containing feed or feed additive product is often stored by the farmers for long periods of time. This storage many times is under conditions where there is some moisture. In many instances there is just enough moisture that the bacteria are activated or start to grow, but yet there is an insufficient amount of moisture to sustain them. As a result they die. Thus, the activity of the direct fed microbial is stopped. In other instances, the addition of antibiotics to the direct fed microbial containing feed or feed additive adversely interacts with the bacteria, particularly if there are small amounts of moisture present and thus again bacteria are killed. Thus, there is a significant problem of long term storage stability for direct fed microbials.

In another environment, where the direct fed microbial is added to, for example chicken feed, it is common to pelletize the material with the direct fed microbial added before pelletizing. Moisture from steam used during pelletization partially activates the bacteria, but may, as a result of insufficient moisture to sustain them, kill them. Also heat during pelletization may kill them. Then, too, there is the problem of the acid environment of the stomach potentially inactivating bacteria before they really reach the intestine. Thus, there is a continuing need for direct fed microbials which will release the organisms only at the proper time in the intestine, without early release due to moisture conditions or adverse pH conditions such as exist in the digestive tract anterior to the small intestine.

It is important to note for purposes of this invention that the free fatty acid does not individually encapsulate and form microcapsules of microorganisms. Instead, the product of the process of the present invention forms microspheres. A microsphere refers to a fatty acid matrix in which a plurality of microorganisms are incorporated. It is different from a microcapsule in which individual organisms are encapsulated. In a microsphere the fatty acid matrix functions for the composite similar to the relationship between a cookie dough matrix and chocolate chip cookies, with the chips representing a group of microorganisms, such as bacteria or yeast. Microcapsules will not work in the process of this invention, whereas microspheres do. Microspheres provide stability advantages and more effective dosing with the microorganisms than individual microencapsulation of each microorganism.

It is a primary objective of the present invention to provide direct fed microbials suitable for animal feed ration addition which contains microorganisms that are contained in microspheres produced in a special rotary process technique, using free fatty acid for formation of the spheres.

Another objective of the present invention is to provide a direct fed microbial which has stability at levels within the range of from 3 months to 6 months without any significant organism count reduction.

Another objective of the present invention is to provide a process of rotary production of microspheres of dried bacteria which provides a matrix of free fatty acid within which a plurality of organisms are contained.

Another objective of the present invention is to provide rotary disc microspheres of dried bacteria which are free flowing, and easily processible with animal feed rations.

An even further objective of the present invention is to provide microspheres of *Enterococcus faecium*, Lactobacilli, and yeast.

SUMMARY OF THE INVENTION

Figure 1:
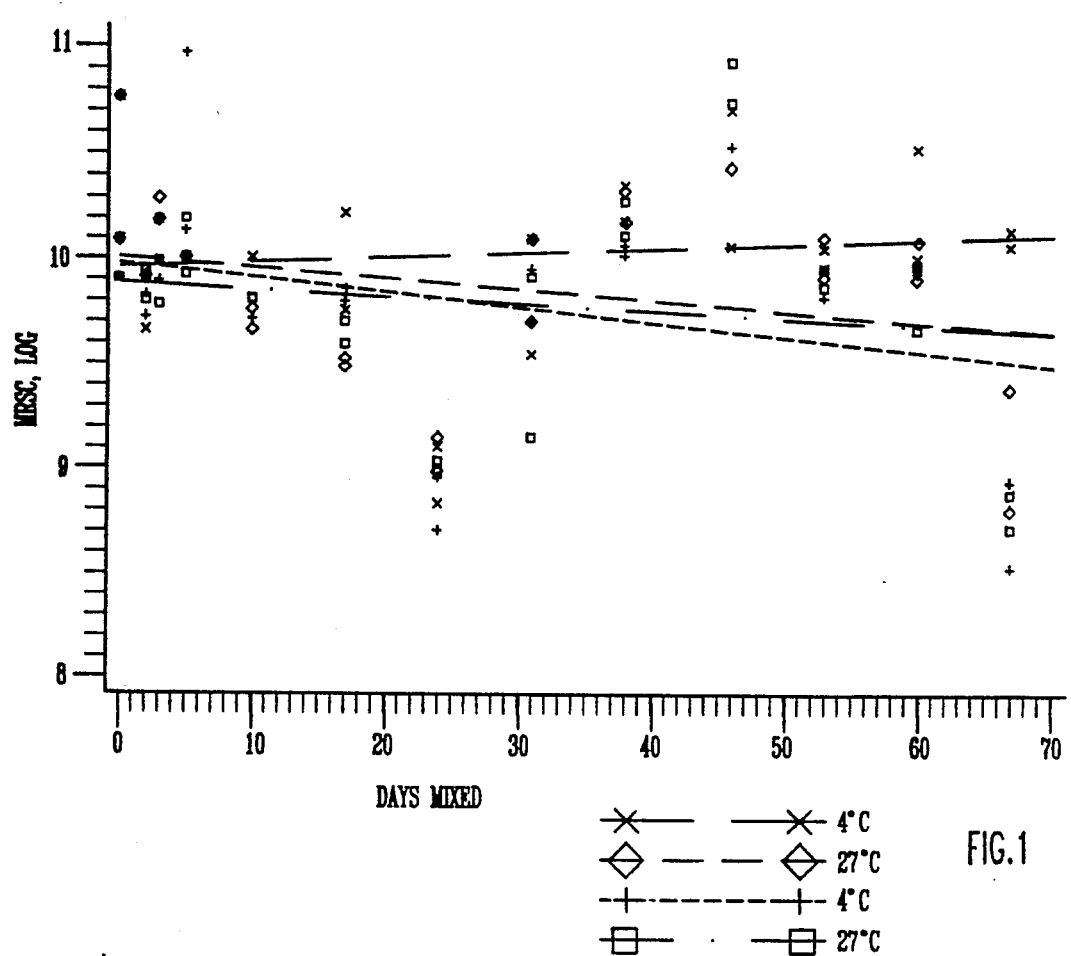
FIGS. 1, 2 and 3 show graphically the stability of microspheres of strains using stearic acid as the free fatty acid.

Microsphere particles of fatty acid matrix containing organisms such as bacteria, preferably stearic acid encapsulated *Enterococcus faecium*, are provided. The process provides, for example, freeze dried bacterial culture in microspheres, achieved by mixing freeze dried bacteria with from 50% to over 90% by weight of a stearic acid melt, and thereafter rotary disc processing. The process, as later explained, is designed to minimize heat risk to the organisms during production.

DETAILED DESCRIPTION OF THE INVENTION

This invention relates to freeze dried, rotary disc microspheres of microorganisms including fungi such as yeast, and also including bacteria. Preferably the organisms are bacteria. There are three significant and important aspects of this invention that distinguish it from other prior patents for encapsulated bacteria. In the first instance it is the nature of the product, i.e, microspheres and in the second instance it is the free fatty acid. In the third instance it is the nature of the rotary disc process. Normal processes use a conventional spray drying technique, not a method of rotary disc production of microspheres. It is the coaction of these three distinct features which provide for the highly stable direct fed microbial of the present invention. If these features are not used, the benefits illustrated by the examples may not be achieved.

The preferred matrix for forming the microspheres is a $C_{12}$ to $C_{24}$ free fatty acid. While mixtures of fatty acids may be employed, it is preferred that a single pure free fatty acid be employed. It is also preferred that the free fatty acid be a saturated fatty acid, with the most preferred being stearic acid.

Generally speaking, it is important that the fatty acid have a melting point less than 75° C., preferably within the range of 40° C. to 75° C. It must, of course, be solid at room temperature in order to be an effective matrix. All free fatty acids falling within the range of chemical description heretofore given will meet these requirements.

The precise microorganism for use in the microspheres is not critical. However, the precise one selected will depend upon the direct fed microbial being formed. Generally speaking, for use in this invention, *Enterococcus faecium* is the preferred bacteria although others can be used. Therefore it should be understood that other bacteria such as Lactobacillus, Bacillus, etc. may also be employed. Mixtures of strains may be employed as well as individual strains. Yeast and fungi may also be used. In order to enhance the product stability for bacteria they are typically freeze-dried and placed in the product. Thus, they can be revived by moisture addition.

In the microspheres, made in accordance with the process discussed below, the particles generally comprise from about 50% to over 90% by weight of the fatty acid component with the balance being microorganisms, usually bacterial culture. The preferred range is from about 60% to about 75% fatty acid. If too little fatty acid is used, the coating will be inadequate for protection. On the other hand, if too much is used, the coating will be too thick and results in inadequate release in the gut.

The microsphere process as used in this invention is a rotary disc process. Generally speaking in the rotary disc technology, a slurry of the microorganisms, often bacteria and fatty acid components are thoroughly mixed with the mixture being added at a uniform rate onto the center of a rotating stainless steel disc. It is there flung outwardly as a result of centrifugal force. It is then collected in a cooling chamber maintained at ambient conditions or slightly lower, sized and readied for packaging.

While rotary disc processing is known, it is not known for use with microorganisms for preparing microspheres. Generally speaking, for descriptions of rotary disc encapsulation of materials, see a paper by Johnsons, et al. of the Southwest Research Institute of San Antonio, in the *Journal of Gas Chromatography*, October, 1965, pages 345-347. In addition, a rotary disc processor suitable for use in this invention is described in detail in United States Letters Patent, Sparks, 4,675,140, issued Jun. 23, 1987 and entitled "Method For Coating Particles or Liquid Droplets", the disclosure of which is incorporated herein by reference.

It is important to note that rotary disc microsphere processing provides a distinctly different product than does conventional tower spray drying. In conventional tower spray drying there is a tendency for particles to cluster, for the coating to be uneven, and thus for the stability of the product to be significantly effected perhaps from days to weeks. When rotary microsphere processing, particularly with the fatty acid agents used in this invention is used, the stability of the resulting microorganisms, particularly bacteria, even when subjected to some moisture and antibiotics, will be for from three to six months.

When the microsphere matrix of free fatty acid material of the present invention is used within the ranges hereinbefore expressed, the process typically employing a 4" rotary disc can be run at the rate of from 2,000 rpm to 4,000 rpm, preferably about 2,500 rpm to 3,200 rpm with a feed rate of from 50 grams to 200 grams per minute. The preferred conditions presently known are use of stearic acid, use of *Enterococcus faecium*, a four inch rotary disc, 3,000 rpm and a feed rate of 100 grams per minute with a bacteria/stearic acid slurry of 35% bacteria, 65% stearic acid. When this is done, a product having a particle size of from 75 microns to 300 microns will be achieved, with a preferred level of less than 250 microns.

Figure 2:
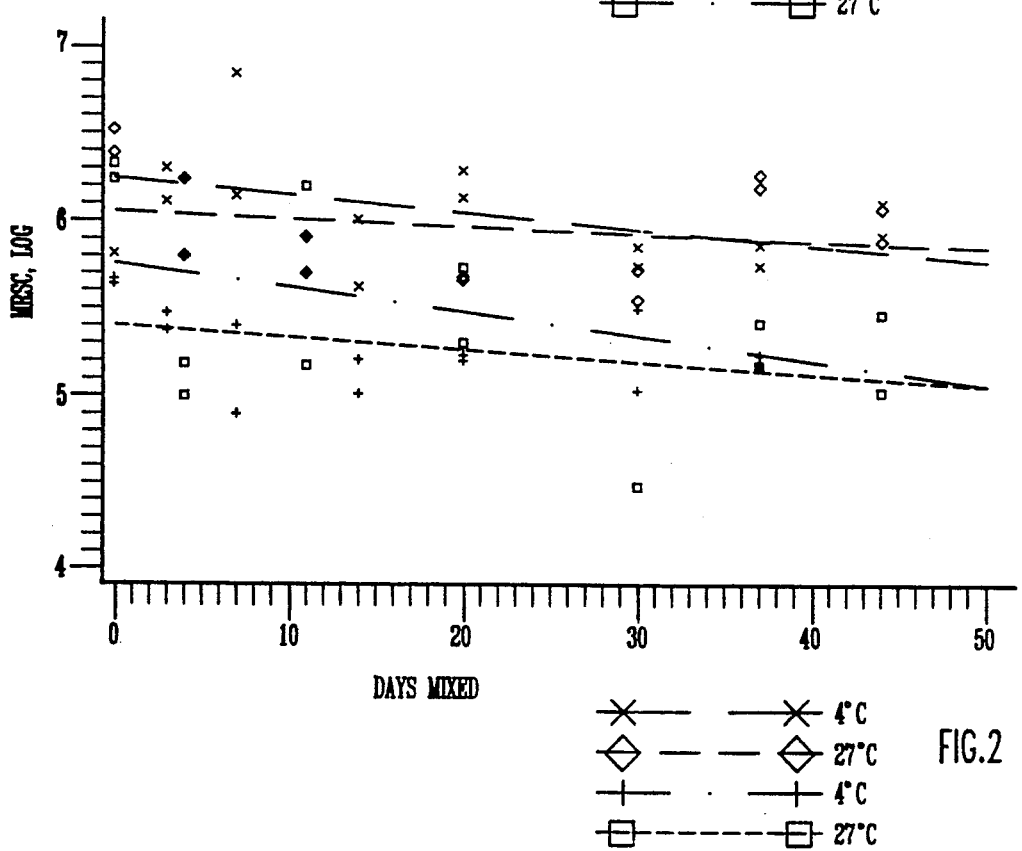
Figure 3:
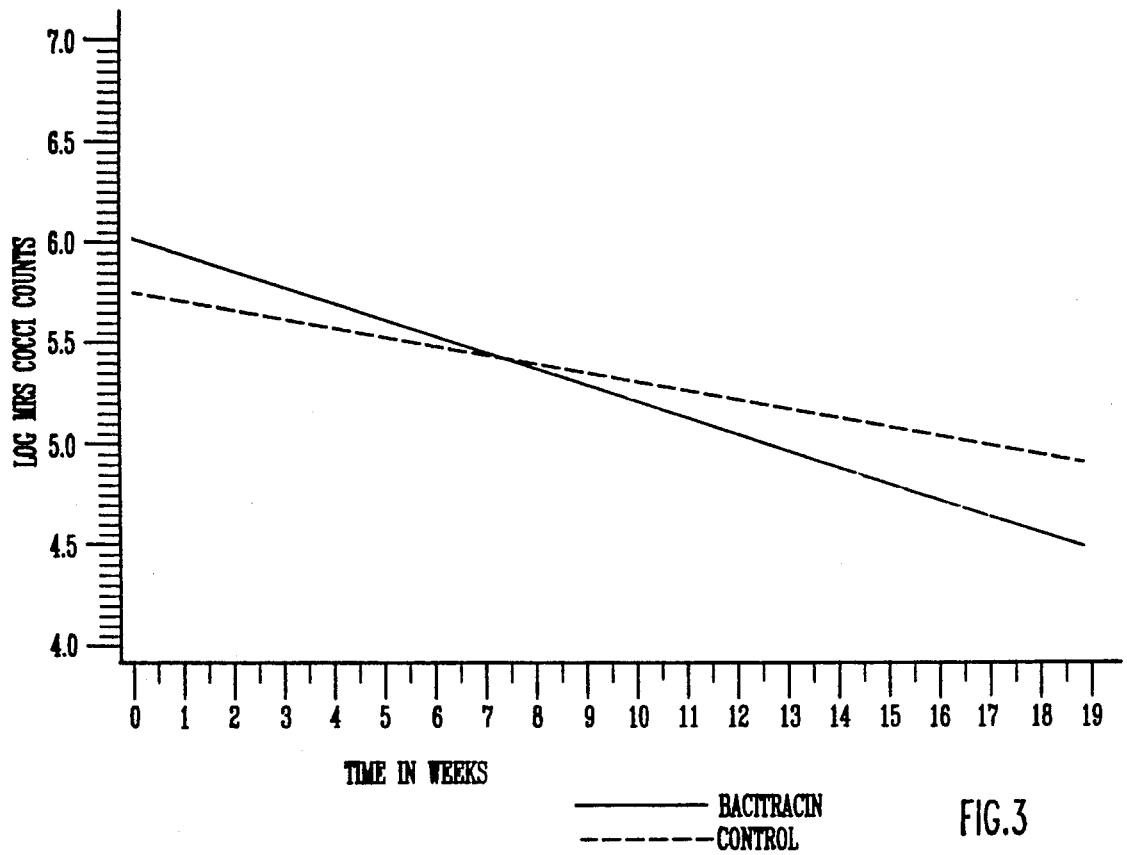

FIGS. 1, 2 and 3 will be described in connection with the examples 1-4.

Figure 4:
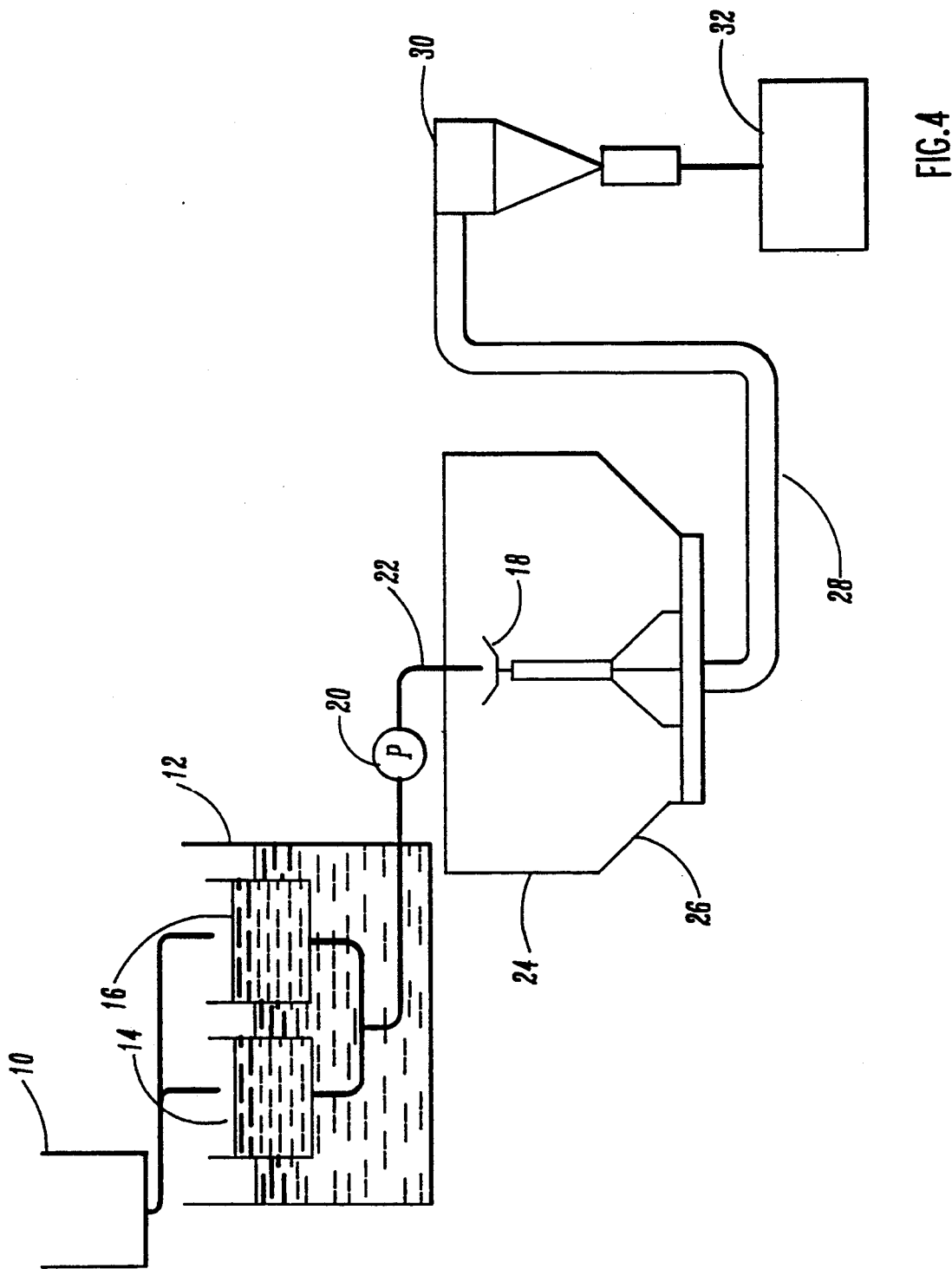
FIGS. 4, 5 and 6 show in block diagram format, schematics for practice of the present invention.
Figure 5:
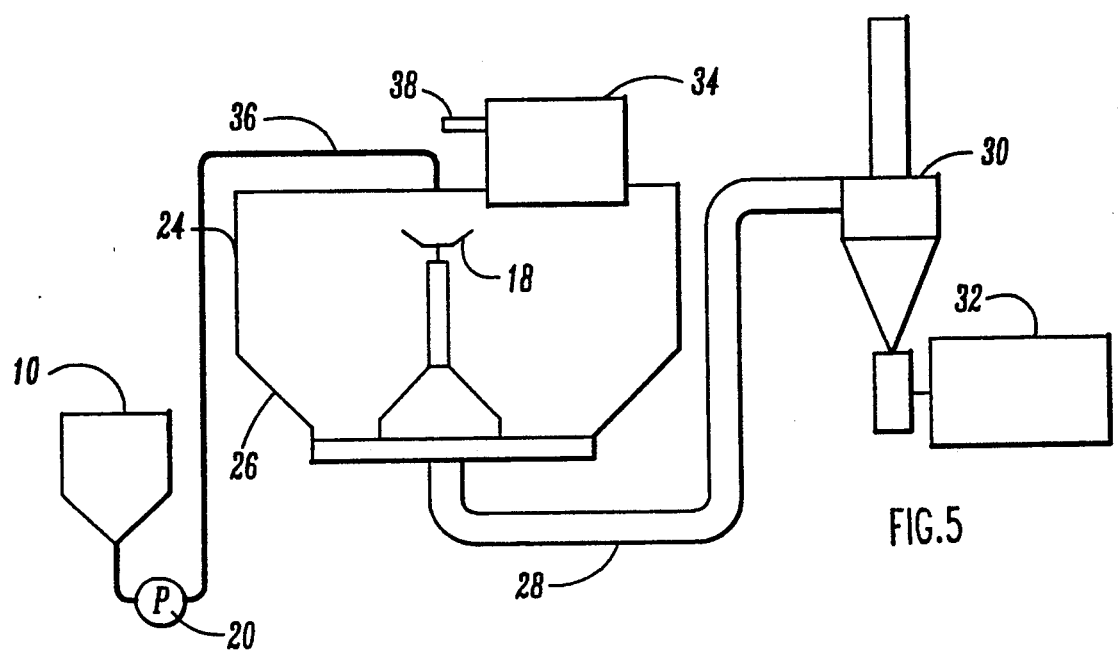
Figure 6:
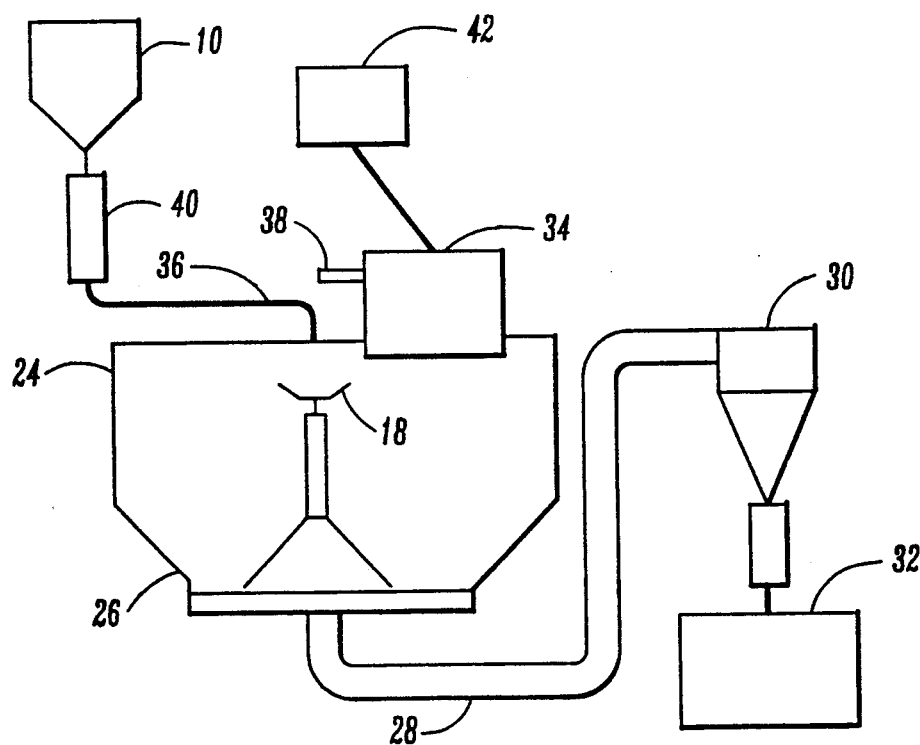

FIGS. 4-6 describe, in schematic format, the preferred aspects of the process of the present invention. In particular, the basic process is similar to that described in the parent application for the production of microspheres. However, a highly preferred option is a separate feeding of culture and molten free fatty acid, which results in the culture being exposed to heat for only very short periods of time.

Figure 7:
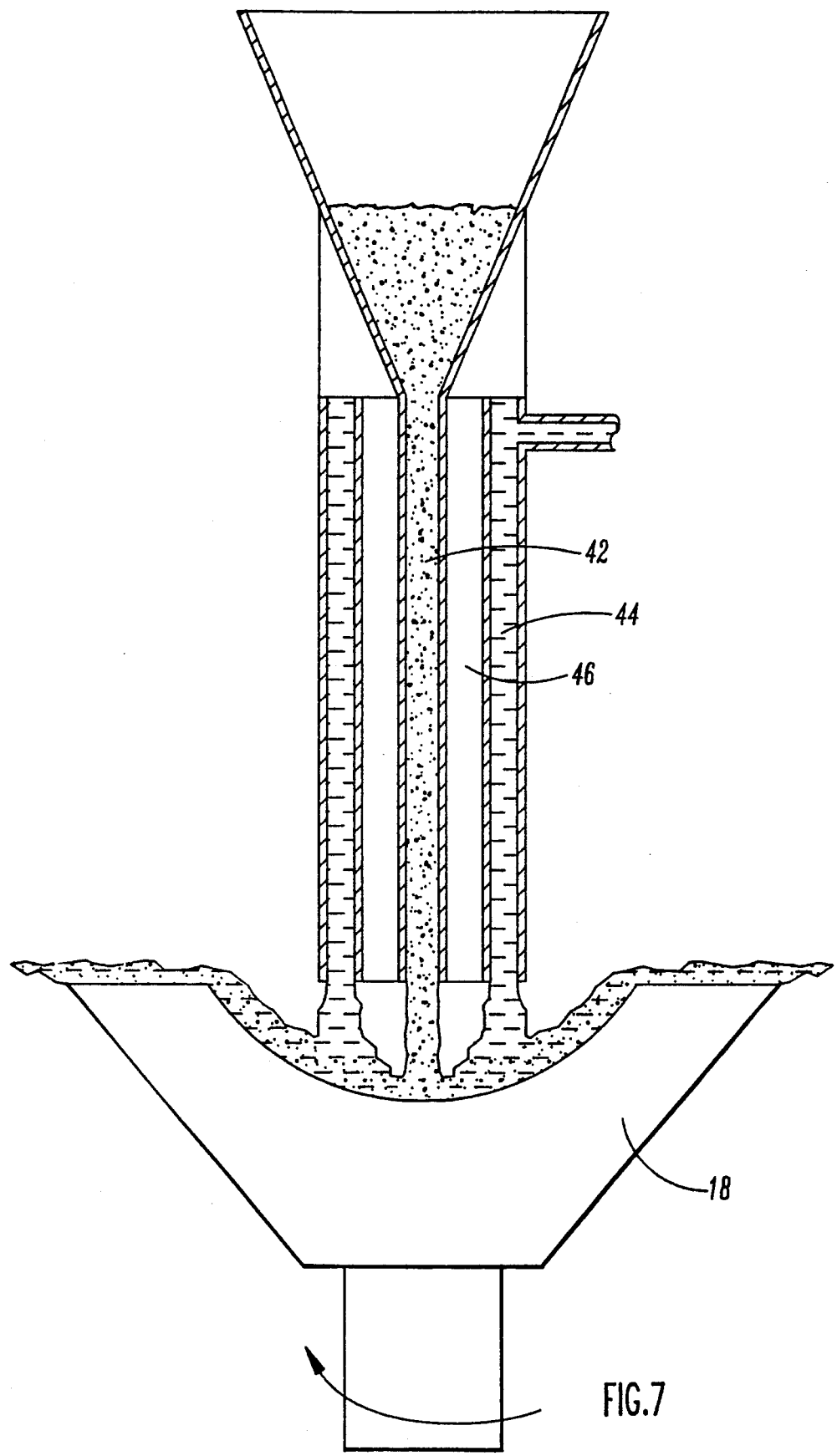
FIG. 7 shows in schematic diagram another feed stream system for use in the invention.

FIG. 7 shows yet another method of separate feed stream technique useful for the present invention.

A further modification to the system includes adding a moisture absorbing column for the molten free fatty acid and a dehumidifier for the bacterial culture chamber. These modifications will increase the recovery of viable microsphered organisms from the process, possibly lowering the cost of production.

FIG. 4 shows the basic process. Stearic acid is placed in the stearic acid melt kettle 10 in amounts sufficient to operate for several hours. It is therein melted. The melted material is then pumped into a smaller mixing vessel 12 wherein the stearic acid 10 is mixed with culture concentrate as illustrated in culture kettles 14 and 16. Culture kettle 12 holds only enough of the mixture to operate for approximately 20 minutes, limiting bacterial exposure to the higher temperature (60° C.) required to keep the matrix molten. A second mixing vessel 16 is operated simultaneously so that when the contents of kettle 14 starts to get low another batch can start mixing in kettle 16. Both kettles 14 and 16 contain mixers (not depicted) to keep the culture distributed evenly. By operating under this type of batch mixing system, a continuous flow may be supplied to the disc 18. Both mixing kettles 14 and 16 are contained in a constant temperature oil bath to insure that the matrix material remains molten during production.

The mixture is pumped by a pump 20 and line 22 into the collection chamber 24. The lower section 26 of the collection chamber 24 is angled so the microspheres will roll down the sides into a collection duct 28 where they are transferred by air movement to the cyclone collector 30. Microspheres are trapped in the cyclone collector 30 and transferred to the sizing sieves 32 where over and undersized particulars are removed to be recycled into the melting vessel 12.

FIG. 5 shows a modification of the basic process of FIG. 4 wherein the culture kettles 14 and 16 in the oil bath are replaced by a continuous culture feeder 34, positioned so that the culture is added to a stream of molten matrix material via line 36, and, as well culture feeder line 38, it goes directly upstream from the disk 18. In this manner, exposure of the culture to the molten matrix is limited to seconds rather than minutes as in the constant temperature bath, with the culture kettles 14 and 16. This will limit heat damage to the bacterial cells.

FIG. 6 shows a further modification of the system in that a moisture absorbing column 40 is added between the stearic acid melting vessel 10 and the point at which the culture is introduced via continuous solid culture feeder 34. Dehumidifier 42 is also added to supply dry air to the culture hopper or collection chamber 24. These modifications, as shown in FIG. 6, remove excess moisture before the microspheres are processed. Again the process of FIG. 6, similar to the process of FIG. 5, takes advantage of premelting of the free fatty acid, and combining of it with the culture just prior to placement on the rotary disc 18, all in an effort to minimize heat exposure. Each of the processes shown in FIGS. 4, 5 and 6 has distinct advantages and use of the processes shown in FIGS. 5 and 6 is especially preferred for heat sensitive materials.

FIG. 7 shows another way of successful formation of microspheres which avoids heat damage to the bacteria. The solids are fed through the inner tube 42 and the liquid fatty acid material is fed through the outer tube 44. A space 46 is left between the two feed streams to prevent contact of the two feed streams until they touch the disk surface 18. As the disk 18 rotates, the solids are projected outward and come in contact with the fatty acid coating material to become coated as they travel to the edge of the rotating disk 18.

This system is particularly useful for making microspheres of heat sensitive material in molten shell materials as the contact time with the shell in melt form is very short.

The following examples are offered to further illustrate, but not limit, the process of the present invention.

EXAMPLE 1

Example 1 correlates with FIG. 1. It shows the product stability of two different strains of *Enterococcus faecium* with temperatures of 4° C. and 27° C. As illustrated in FIG. 1, it shows a stability of the microspheres of strains of *Enterococcus faecium*, with the process being by the rotary disc using stearic acid with a level of 35% culture weight. The method is that illustrated in FIG. 4. Conditions were as previously described herein, namely a 35/65 bacteria stearic acid slurry at a temperature of 60° C., using a four inch rotary disc, operating at 3,000 rpm and a feed rate of 100 grams per minute. The culture was coated in matrix to form a microsphere, placed in heat sealed vapor barrier pouches and destructively sampled weekly for CFU determination. It can be seen that the product of the invention maintained excellent organism colony forming unit (CFU) counts out to storage times at long as 70 days.

EXAMPLE 2

Example 2 is to be interpreted in connection with FIG. 2. The FIGURE shows the stability of individual encapsulated strains when mixed in a typical feed ration in the presence of three poultry antibiotics. The ration consisted of the following:

| | |
|---|---|
| 54% | fine cracked corn |
| 26% | soybean meal |
| 2% | fish meal |
| 1.5% | dicalcium phosphate |
| 1% | limestone |
| 5.5% | soy oil |
| 12% | moisture content |

Three antibiotics were added at the following inclusion rates by weight: Deccox 6% (454 ppm), Salinomycin (50 ppm) and monensin sodium (120 ppm).

Culture was added to the mixture at a level to deliver approximately $1\times10^6$CFU/gm feed. Feed was packaged in heat sealed bags and incubated at room temperature. Samples were taken weekly for CFU determination. The graph of FIG. 2 illustrates the excellent stability.

EXAMPLE 3

Example 3 is to be interpreted in conjunction with FIG. 3. It shows the stability of the encapsulated *Enterococcus faecium* mixture in feed in the presence of different antibiotics. The ratio consisted of 60% fine cracked corn, 38% soybean meal and 2% limestone with a moisture content of about 14%. Culture was added to a level of approximately $10^6$ CFU/gm feed and mixed. Ten pound aliquots were stored in sealed bags at 20° C. and sampled weekly for 16 weeks. The antibiotics were included in the ration at the following levels:

| | |
|---|---|
| Bacitracin methylene disalicylate | 50 gm/ton |
| Carbadox | 50 gm/ton |
| Chlortetracycline | 200 gm/ton |
| Lasalocid | 30 gm/ton |
| Lincomycin | 100 gm/ton |
| Neomycin | 140 gm/ton |
| Oxytetracycline | 150 gm/ton |
| Sulfaethazine | 100 gm/ton |
| Tylosin | 100 gm/ton |
| Virginiamycin | 20 gm/ton |
| ASP250 | 100 gm/ton |

Table 1 is a list of the minimum times for a 1 log loss in colony forming units (CFU).

TABLE 1

Time in days for loss of 1 log CFU counts at 20 C. in 14% moisture mash feed.

| Antibiotic | Time of Storage (days) |
|---|---|
| Control | 103 |
| Bacitracin | 88 |
| Carbadox | 54 |
| Chlortetracycline | 60 |
| Lasalocid | 57 |
| Linocomycin | 75 |
| Neomycin | 53 |
| Oxytetracycline | 59 |
| Sulfamethazine | 62 |
| Tylosin | 52 |
| Virginianycin | 112 |
| ASP250 | 67 |
| Furadox | 53 |

EXAMPLE 4

In Example 4 the stability of product after pelletizing for use of a chicken feed product was determined. The microencapsulation conditions were as earlier described. The conditions used in this study were the following:

| | |
|---|---|
| Crude Protein, not less than | 18.0% |
| Crude Fat, not less than | 5.0% |
| Crude Fiber, not more than | 6.0% |

The pellets with and without the antibiotic (CTC 50 gm/ton) were made with the following ingredients and conditions.

Corn, SBM, whey, soy oil, dicalcium phosphate, limestone, trace mineral premix, vitamin premix, selenium, copper sulfate. Culture was added at approximately $5 \times 10^5$ CFU/gm feed (100-150 gm/ton).

Conditioning temperature was 70° C. and the pellets out of the dye were 78° C.

Pellets were stored in unsealed bags and sampled weekly for CFU determination.

In each instance the pelletized product was not adversely affected in stability by the conditions of pelletizing. In particular, the pelletized product showed stability equal to the unpelletized product.

EXAMPLE 5

Example 5 illustrates running the process as described in example 1, except that the strain of *Enterococcus faecium* is removed and the microspheres involving stearic acid as a free fatty acid coating yeast. Table 2 shows the results.

The microspheres produced from the process and illustrated in Table 2 contained yeast with a viable cell count as shown in the table. They were stored at ambient temperature 84 days. At the end of the storage period, viable yeast cells were assayed. On day 84 the viable yeast count in the microspheres was $1.3 \times 10^9$ CFU per gram. Slightly higher recovery is due to the normal variation in sampling and assaying microspheres. A sample of the yeast containing microspheres (0.841 gm) was mixed with 2,270 gm of a typical poultry ration and stored at ambient temperature. The poultry ration contained 17% moisture and was prepared as earlier described in example 2.

Based on the initial counts of the microspheres of $5.3 \times 10^8$ CFU per gram, the calculated dilution rate gave a count of $1.96 \times 10^5$ CFU per gram. After storage for 84 days the feed was assayed for viable yeast cells. On day 84 the yeast cell count was $7 \times 10^4$ CFU per gram of feed.

EXAMPLE 6

The microsphere process shown in example 1 is run with the following modification:
1) Strains from the Genus Lactobacillus and of the species *L. plantarum* or *L. caseii;*
2) Bacterial culture are prepared at an inclusion rate of between 2 and 40%, preferably about 30%.
3) Bacterial culture is introduced into the molten stearic acid just prior to contact with the spinning disk, as outlined in FIG. 4.
4) Care should be taken to protect the bacterial culture from high humidity, for example greater than 40%, during storage and processing, by using the modification of FIG. 5.
5) Care should be taken to maintain the air temperature at about 80° F. or less and the humidity in the microsphere collection area at about 60% or less.

Further experiments such as those listed in example 2 can be run with microsphering of the genus Lactobacillus and species *L. plantarum, L. acidophilus* or *L. caseii.* In such processing, it is expected that the microsphered organisms shall maintain excellent survival with loss of viability at less than one log of colony forming units (CFU) to storage times, up to as long as 70 days. It is also expected that the microsphered organisms, when mixed with a typical poultry ration, will maintain excellent survival with losses of viability to be less than one log of CFU to storage time, up to as long as 45 days.

What is claimed is:

1. A process of preparing discrete individual fatty acid matrix microspheres of microorganisms said microorganisms dwelling in a fatty acid matrix, said process comprising:
   preparing a first feed stream of fatty acid melt of a $C_{12}$ to $C_{24}$ fatty acid,
   preparing a second feed stream of microorganism culture,
   feeding separately said culture feed stream and said fatty acid melt feed stream into a rotary disc processor to provide a mixture which is from 50% to about 90% by weight of said fatty acid melt, and
   rotary disc microsphere processing said mixture in a rotary disc processor to provide free-flowing fatty acid matrix microspheres of organisms.

2. The process of claim 1 wherein the rotary disc is operating at an rpm within the range of 2,000 rpm to 4,000 rpm.

3. The process of claim 1 wherein the rotary disc is operating at a range of from 2,500 rpm to 3,200 rpm.

4. The process of claim 1 wherein feed rate of material into the rotary disc processor is from 50 grams per minute to 200 grams per minute.

5. The process of claim 1 wherein the fatty acid is stearic acid.

6. The process of claim 1 wherein the first feed and second feed are kept separate until the feeds contact the disc.

7. The process of claim 1 wherein the first feed and second feed contact each other for a short time sufficient to preserve microorganism viability prior to contacting the disc.

8. The process of claim 7 wherein the first and second feed contact each other for less than one minute prior to contacting the disc of said rotary disc processor.

9. The process of claim 1 wherein the microorganism is *Enterococcus faecium.*

* * * * *